United States Patent
Carpentier et al.

(10) Patent No.: US 6,231,602 B1
(45) Date of Patent: May 15, 2001

(54) AORTIC ANNULOPLASTY RING

(75) Inventors: Alain Carpentier, Paris (FR); Hung Ly Lam, Norco; Than Nguyen, Tustin, both of CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 0 days.

(21) Appl. No.: 09/293,215

(22) Filed: Apr. 16, 1999

(Under 37 CFR 1.47)

(51) Int. Cl.$^7$ .................................................... A61F 2/24
(52) U.S. Cl. ............................................... 623/2.36
(58) Field of Search ................... 623/2.1, 2.17, 623/2.18, 2.19, 2.22, 2.23, 2.36, 2.37, 2.38, 2.42

(56) References Cited

U.S. PATENT DOCUMENTS

| | | | |
|---|---|---|---|
| 3,570,014 | 3/1971 | Hancock | 3/1 |
| 3,656,185 | 4/1972 | Carpentier | 3/1 |
| 3,714,671 | 2/1973 | Edwards et al. | 3/1 |
| 3,755,823 | 9/1973 | Hancock | 3/1 |
| 4,035,849 | 7/1977 | Angell et al. | 3/1.5 |
| 4,055,861 | 11/1977 | Carpentier et al. | 3/1.5 |
| 4,106,129 | 8/1978 | Carpentier et al. | 3/1.5 |
| 4,343,048 | 8/1982 | Ross et al. | 3/1.5 |
| 4,388,735 | 6/1983 | Ionescu et al. | 3/1.5 |
| 4,489,446 | 12/1984 | Reed | 3/1.5 |
| 4,501,030 | 2/1985 | Lane | 3/1.5 |
| 4,506,394 | 3/1985 | Bédard | 3/1.5 |
| 4,605,407 | 8/1986 | Black et al. | 623/2 |
| 4,666,442 | 5/1987 | Arru et al. . | |
| 4,778,461 | 10/1988 | Pietsch et al. | 623/2 |
| 4,816,029 | 3/1989 | Penny, III et al. | 623/2 |
| 4,917,698 | 4/1990 | Carpentier et al. | 623/2 |
| 5,032,128 | 7/1991 | Alonso . | |
| 5,104,407 | 4/1992 | Lam et al. . | |
| 5,258,021 | 11/1993 | Duran | 623/2 |
| 5,824,069 | 10/1998 | Lemole . | |
| 5,855,601 | 1/1999 | Bessler et al. . | |

FOREIGN PATENT DOCUMENTS

| | | |
|---|---|---|
| 0125393B1 | 12/1987 | (EP) . |
| 0150608B1 | 6/1988 | (EP) . |
| 0196116B1 | 1/1990 | (EP) . |
| 0143246B1 | 11/1991 | (EP) . |
| 0257874B1 | 4/1992 | (EP) . |
| 0375181B1 | 2/1993 | (EP) . |
| 1264472 | 2/1972 | (GB) . |
| 2056023A | 3/1981 | (GB) . |
| 2159242A | 11/1985 | (GB) . |
| 2206395A | 1/1989 | (GB) . |
| WO 83/02225 | 7/1983 | (WO) . |
| WO 90/09153 | 8/1990 | (WO) . |

*Primary Examiner*—David J. Isabella
(74) *Attorney, Agent, or Firm*—Debra D. Condino; Guy L. Cumberbatch

(57) ABSTRACT

An infra-annular annuloplasty prosthesis is disclosed including a flexibly semi-rigid frame, a portion of which is shaped to conform to the scalloped configuration of the normal circumference of an arterial heart valve annulus. Axially projecting legs spaced circumferentially to correspond to the location of tissue adjacent to the valve commissures are provided for support and anchoring of the annulus-conforming portion to the dense fibrous tissues adjacent each commissure. The prosthesis includes a one-or two-part frame having scalloped upper and lower edges defining peaks and valleys. The upper edge is shaped to follow the contour of the tissue underneath the valve leaflets, and thus supports the leaflets and aortic wall from below. The lower edge is similarly scallop-shaped, but with less pronounced peaks and valleys than the upper edge, and is thus shaped to conform to the aortic annulus shape and provide support directly thereto.

11 Claims, 3 Drawing Sheets

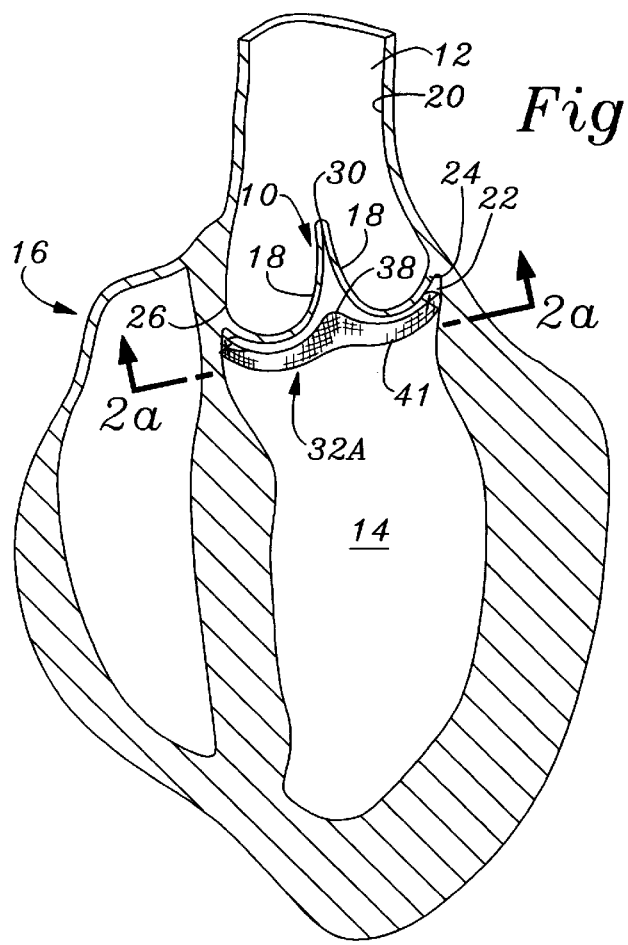
Fig-1a
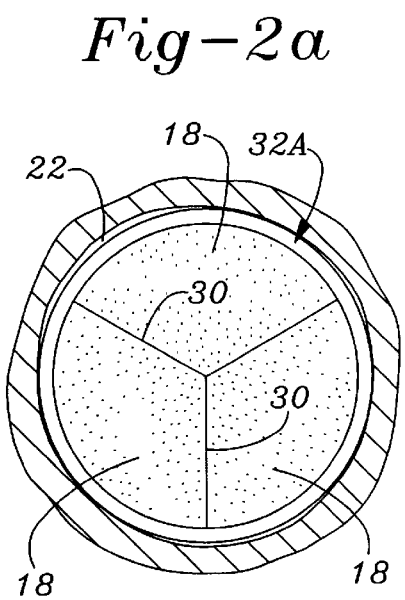
Fig-2a
Fig-2b
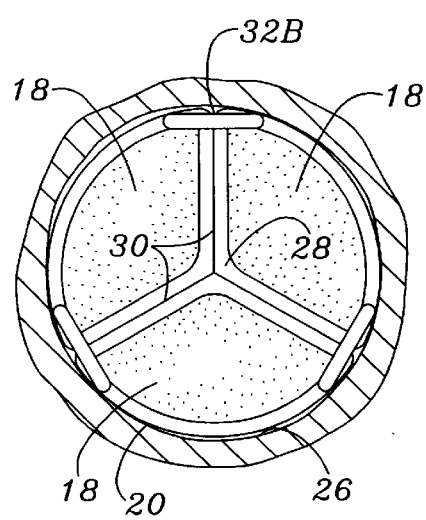
Fig-1b
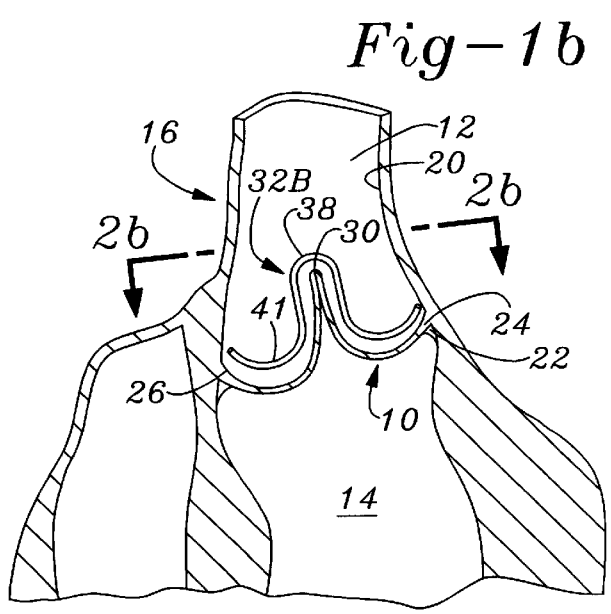

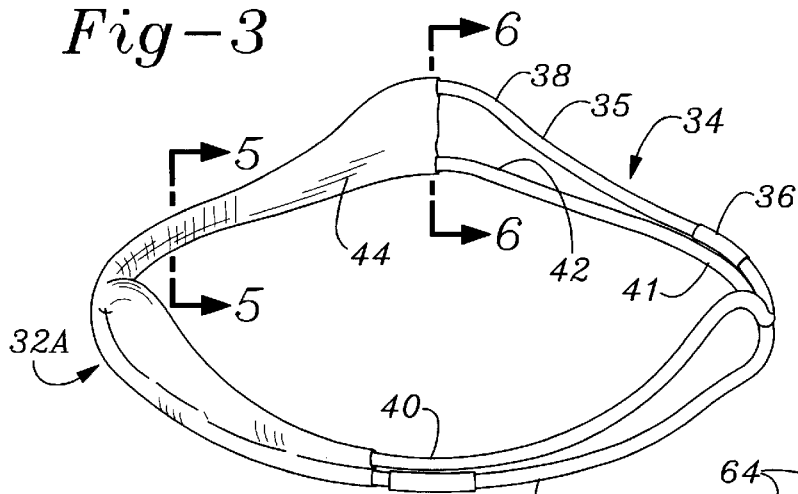
Fig-3
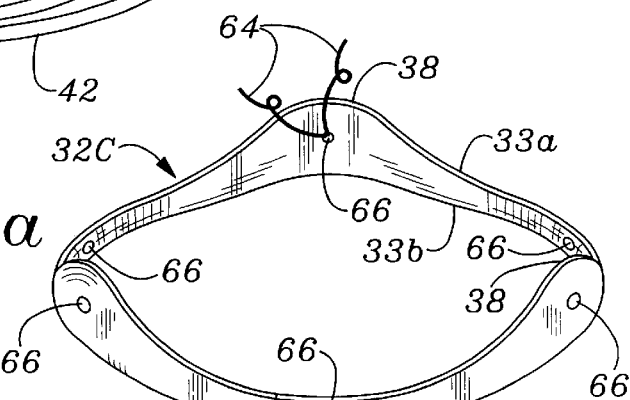
Fig-3a
Fig-4
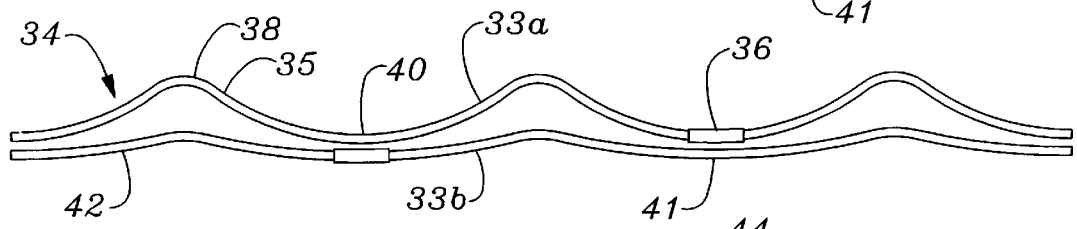
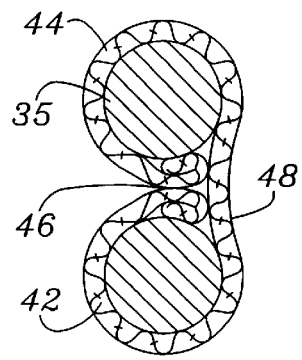
Fig-5
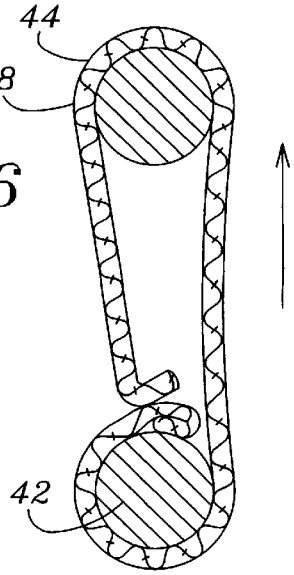
Fig-6

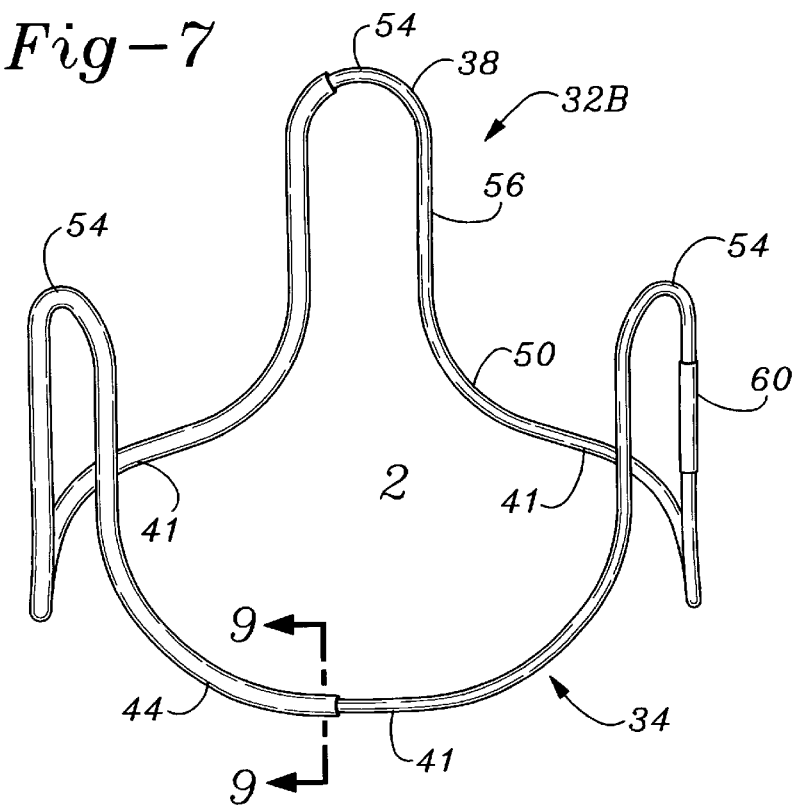
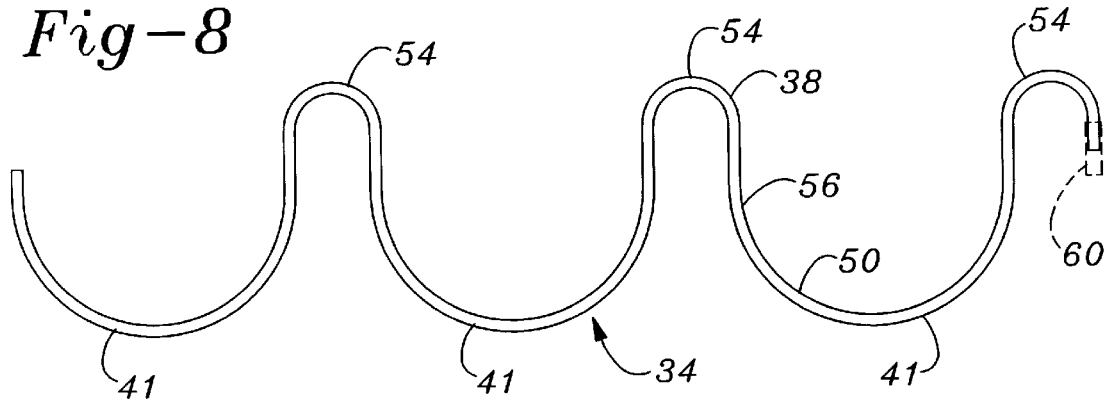
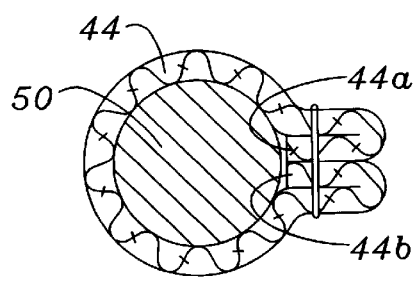
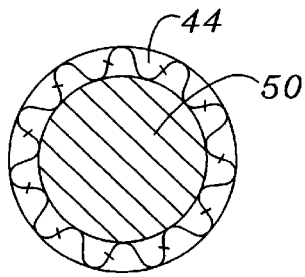

AORTIC ANNULOPLASTY RING

FIELD OF THE INVENTION

The present invention relates generally to valvuloplasty prostheses, and more particularly to biocompatible rings for constricting and restoring the annulus of a natural aortic or pulmonary trileaflet valve.

BACKGROUND OF THE INVENTION

The aortic and pulmonary valves, collectively known as arterial valves, are located respectively in the left and right ventricles of the heart. They serve to prevent regurgitation of blood from the aortic artery or pulmonary artery into its associated ventricle when that ventricle is in its expanded state. Both valves consist of three semicircular leaflets or flaps attached by their convex margins to the wall of the artery at its junction into the ventricle. In both the aortic and pulmonary valves, the straight border of each leaflet is free and directed upward into the artery.

Although the aortic (left ventricle) valve is larger, thicker and stronger than the pulmonary (right ventricle) valve, the openings of both arteries into their ventricles are generally circular, and form an annulus or ring that is composed of fibrous rather than muscular tissue. Another characteristic shared by these valves is the presence of pouches or sinuses one behind each leaflet, that exist between the valve and the wall of the artery. The blood, in its regurgitation back toward the ventricle, finds its way into these sinuses, and so closes the valve-flaps.

Healthy functioning valves such as, for example, the aortic valve require a secure meeting of the leaflet free borders along the lines at which they come together. When these free borders securely meet so that no blood can escape back into the ventricle, this positive closing of the leaflets is called coapting. The regions extending along and adjacent to the arterial wall at which the leaflets "coapt" are called commissures. In a properly functioning valve, the circular annulus (defining the border between the sinuses of the ascending vessel and the ventricle) provides a firm base ring for the convex margins or "cusps" of the leaflets so that their free borders can meet securely. A common defect leading to aortic valve dysfunction is a dilation or stretching of this arterial annulus, and often its associated valve sinuses, preventing positive closure of the attached leaflets and possibly even allowing one or more leaflets to flip over, or "prolapse", toward the ventricle. Total valve replacement is one solution to valve dysfimction, but repair of the annulus or sinuses by various techniques, thereby retaining the natural valve, is preferred.

Among such techniques for reconstructing the aortic annulus is the practice of drawing in the stretched annulus by means of sutures threaded along the dilated circumference of the annulus. The success of such a technique varies significantly with the skill of the surgeon, and the technique may produce inconsistent circumferential pleats, which would adversely affect desirable annular symmetry. An alternative to the all-suture technique of annular reconstruction is the use of a prosthesis to restore the normal circumference of the annulus. Correction by a prosthesis is potentially longer-lasting than is the all-suture technique, since after the latter procedure, tissues will tend to compensate against abnormal pressure by the sutures, possibly defeating the purpose of the repair. A prosthesis has the additional advantages of providing the predictability of a defined structure, and of enabling the surgeon to determine the ultimate outcome of the procedure before closure, i.e., without having to wait for post-operative analysis.

However, much of the prior art devoted to annular prostheses has been directed to the reconstructing of the atrioventricular mitral bileaflet and tricuspid trileaflet valves whose specific non-circular configurations are not similar to those of the aortic or pulmonary valves. Accordingly, these prior art prostheses are not suitable for the restoring of an aortic or pulmonary annulus because, unlike the circular aortic or pulmonary valve annuluses, a mitral valve or tricuspid valve annulus is decidedly D-shaped. The mitral and tricuspid annuluses include straight segments formed of dense tissue so that their arcuate portions are relatively more subject to problem elongation. Thus, for their reconstruction, these valves require certain prostheses that are typically anchored to the fibrous straight section of the annulus in order to reconfigure the elongated arcuate portion. For example, U.S. Pat. No. 3,656,185 to Carpentier discloses a mitral valve reconstruction annular prosthesis. It relies on securing its rigid portion to the mitral valve annulus straight segment, and is not compatible with the circular shape of the aortic annulus which lacks this rigid foundation upon which to anchor the prosthesis. Moreover, such rigid attachment to the annulus tends to detrimentally inhibit the natural movement of the annulus during a cardiac cycle of expansion and contraction.

Other annular prostheses such as that described in U.S. Pat. No. 4,489,446 to Reed are also configured to attach to the unique physical aspects of the non-circular atrioventricular valve annulus. Specifically, Reed utilizes reciprocating members which are sutured to the relatively more dense muscular structure of the mitral or tricuspid annulus as contrasted with the weaker fibrous composition of the aortic annulus. In addition, the reciprocating members of Reed are configured for implantation below the valve, not for positioning within the artery as would be desirable in order to reconstruct dilated valve sinuses.

A prosthesis which does not rely on the distinctive shape of the mitral annulus, and thus may be suitable for reconstruction of an aortic annulus, is disclosed in U.S. Pat. No. 4,917,498 to Carpentier. It comprises a ring of many linearly connected segments which depends for its structural integrity on a fabric holding the chained elements together. Such a prosthesis avoids the mitral valve-specific shortcomings of the previously noted atrioventricular prostheses but, because it is configured for attachment to annulus tissue, it is similarly unsuitable for intra-arterial positioning, i.e., above the valve as opposed to below it. This severely limits its ability to reconstruct the aortic valve annulus by beneficially constricting the dilated sinuses that are disposed within the artery.

Accordingly, it is an object of this invention to provide a prosthesis specifically directed to safely, consistently and durably restoring the generally circular shape of an aortic annulus to produce positive valve closure.

It is another object to provide a prosthesis that is simple to manufacture in a range of sizes corresponding to the range of normal valve annulus diameters.

It is a further object to provide a prosthesis rigid enough to maintain a functional annular shape yet flexible enough to allow natural movement of the annulus during the cardiac cycle.

It is a still further object to provide the choice of positioning the prosthesis of this invention below the aortic valve or alternatively above the valve within the walls of the artery.

SUMMARY OF THE INVENTION

These and other objectives are achieved by the present invention which is directed to an arterial annuloplasty prosthesis and associated methods used to restore the generally circular shape of a dilated arterial valve annulus in order to produce positive valve closure. This invention corrects the dysfunction caused by excessive dilation of the aortic or pulmonary trileaflet valve annulus, while allowing for natural movement of the annulus during the cardiac cycle. The apparatus of the present invention does not require complex fabrication, can be made in a variety of desirable diameters and axial heights, and results in a longer-lasting restoration of the dilated annulus. In addition, the implantation method of this invention is less complicated than that of previous techniques allowing the surgeon to verify the success of the restoration before closure of the incision.

Since the aortic trileaflet valve is more likely to require repair than is the pulmonary trileaflet valve, the discussion herein will be directed to repair of the aortic valve. However, it will be understood that the principles discussed with respect to the restoration of the aortic valve annulus apply equally as well to a pulmonary annulus restoration. Similarly, although valves with three leaflets are described, the discussion also applies in principle to those having two leaflets. Accordingly, the present invention is not restricted to the reconstruction of three leaflet aortic valves, but may be applied to any suitable valve having two or more leaflets.

Unlike valve support structures, or stents, the present invention is not intended to provide support to elements of transplanted valves, but rather to restore the size and shape of the natural valve annulus. In practice, a surgeon encountering a dysfunctional yet otherwise competent natural valve, having determined by diagnostic means such as echo doppler that regurgitation of blood into the ventricle is occurring, may decide that the valve leaflets of the valve are not coapting (i.e., meeting in closure) because of excessive elongation of the valve annulus.

To remedy this dysfunction, the present invention provides the surgeon with the choice of a prosthesis appropriately configured for infra-annular or for supra-annular implantation, depending on the specifics of the individual case. For example, where relative ease of implantation is paramount, the supra-annular prosthesis is preferred. Alternatively, where the presence of a complete ring at the site of dilation is important, the infra-annular prosthesis may be preferred.

For either implantation, the present invention provides a flexibly semi-rigid frame having a diameter within the range of normal valve annulus diameters between 17 mm and 29 mm. The frame is dimensioned to conform to the scalloped configuration of the desired or normal circumference of the annulus. Each frame employs three legs projecting axially from the frame for suturing support, with the height of the legs depending on the surgeon's choice of infra- or supra-annular implantation. Typically, the surgeon will have available on site a number of such prostheses with a variety of diameters and leg heights from which to choose.

In addition, the frame of either embodiment is completely covered by a flexible biocompatible material or fabric. This material isolates the frame within the body and facilitates the suturing of the frame to the anchoring fibrous tissues of the heart as opposed to the more rigid muscular tissue of the mitral valve. Preferably, the flexible material should be as thin as possible to avoid overall bulk of the prosthesis and to minimize obstructing the flow of blood from ventricle to artery. A suitable flexible covering may be, for example, polytetrafluoro-ethylene (PTFE), polyester such as polyteraphthalate or similar material. Further, flexible coverings other than PTFE may be used as the isolating and anchoring material with or without a PTFE coating. A woven fabric is preferable for strength with minimal thickness and is more desirable than, for example, a more bulky double velour.

For those applications involving implantation of the prosthesis below the aortic valve, or "infra-annular," the prosthesis includes a one- or two-part frame having scalloped upper and lower edges defining peaks and valleys. The upper edge is shaped to follow the contour of the tissue underneath the valve leaflets, and thus supports the leaflets and aortic wall from below. The lower edge is similarly scallop-shaped, but with less pronounced peaks and valleys than the upper edge, and is thus shaped to conform to the aortic annulus shape and provide support directly thereto.

One embodiment of the infra-annular prosthesis utilizes a two-part wire frame, with one part or wireform above the other, and the wireforms maintained in place relative to each other by the flexible covering material. For infra-annular use, the lower wireform is shaped to conform to the normal circumference of the valve annulus and is flexible enough to permit normal annular flexures yet rigid enough to effectively constrict the dilated annulus to a normal diameter. The upper wireform has essentially the same diameter as the lower wireform and follows its radial contours, but unlike the lower wireform it is provided with an axially projecting leg corresponding to the location of each valve commissure. The legs of the upper wireform project above the lowest point of the prosthesis to a height on the order of 15% to 60% of the prosthesis diameter depending on the surgeon's predetermined or contemporaneous operational requirements, and the legs constitute supports for suturing the covered frame prosthesis to the dense tissue immediately below the commissure-arterial wall intersection. The lower wireform provides the main reconstructive presence of a solid ring for constricting the annulus and restoring its normal diameter.

Where implantation of the prosthesis above the valve is desired, a single wireform is provided. This wireform is a ring having arcuate circumferential segments shaped to conform to individual sinuses or pockets between the valve leaflets and the aortic wall, and three circumferentially spaced legs projecting above the lowest part of the prosthesis to a height on the order of 60% to 120% or more of the prosthesis diameter. The wireform pulls in the dilated sinus tissue, restoring the normal circumference of the valve. For such supra-annular use, the legs of this embodiment have inverted U-shaped apices which fit over the commissure-arterial wall intersections. This construction beneficially allows the legs to be sutured to the denser arterial tissue above the commissure intersection points, thereby securing the prosthesis to the wall of the artery.

The upper portion of this wireform, comprising the legs, is more rigid than are the lower circumferential segments. This differential rigidity has the desirable effect of establishing the securely sutured legs as a firm support structure, preventing the necessarily more flexible lower segments from bowing out. In this way, the sinuses are free to flex and at the same time to maintain their repaired circumferential size.

The present invention advantageously constricts the dilated valve tissue and restores the circular configuration of the aortic annulus while overcoming the problem of excessive rigidity which prevents normal action of the reconstructed tissue. In addition, the present invention has the advantage of unitary construction as contrasted with known multi-segmented prostheses such as the previously described Reed '446 and Carpentier '498 apparatus which require more complex manufacture, and which are unable to accommodate supra-annular as well as infra-annular implementation.

The above and additional advantages of the present invention will be apparent from a reading of the following detailed description of exemplary embodiments of the invention taken in conjunction with the following drawing figures, in which:

BRIEF DESCRIPTION OF THE DRAWINGS

FIGS. 1a and 1b are sectional views of a human heart illustrating emplacement of exemplary infra-annular and supra-annular embodiments, respectively, of the present invention.

FIG. 2a is a sectional view taken along line 2a—2a of FIG. 1a showing a reconstructed aortic valve annulus and further illustrating an exemplary infra-annular embodiment of the present invention.

FIG. 2b is a sectional view taken along line 2b—2b of FIG. 1b showing reconstructed aortic valve sinuses and further illustrating an exemplary supra-annular embodiment of the present invention.

FIG. 3 is an isometric view of an infra-annular prosthesis of the present invention.

FIG. 3a is an isometric view of an alternative infra-annular prosthesis corresponding to that of FIG. 3.

FIG. 4 is a developmental lay-out view of the internal wireforms of the apparatus of FIG. 3.

FIG. 5 is a sectional view taken at line 5—5 of FIG. 3 illustrating a line of minimum separation between the wireforms of FIG. 3.

FIG. 6 is a sectional view taken at line 6—6 of FIG. 3 illustrating a line of maximum separation between the wireforms of FIG. 3.

FIG. 7 is an isometric view of an exemplary supra-annular prosthesis of the present invention.

FIG. 8 is a developmental lay-out view of the internal wireform of the apparatus of FIG. 7.

FIG. 9 is a sectional view taken at line 9—9 of FIG. 7 illustrating the flexible material covering the wireform of FIG. 7.

FIG. 10 is a sectional view similar to FIG. 9 illustrating an alternative configuration of flexible material covering the wireform of FIG. 7.

DETAILED DESCRIPTION OF EXEMPLARY EMBODIMENTS

Turning first to the operating environment of the present invention, FIGS. 1a and 1b illustrate the location of a natural aortic trileaflet valve 10 situated at the base of the aorta 12 between aorta 12 and the left ventricle 14 of a heart 16. Each of the three valve leaflets 18 is attached to the aortic wall 20 immediately above annulus 22, forming a generally circular attachment margin 24. The circumference of annulus 22 conforms generally to the scalloped shape of the continuous circle segments called sinuses 26 that are disposed immediately above the leaflet attachment margin 24. The relationship between the sinuses and the leaflets is more clearly seen in the plan view of FIG. 2b, wherein the pockets or sinuses 26 are shown interposed between leaflets 18 and aortic wall 20. Leaflets 18 are shown in the closed (diastolic) position, and when viewed from above as in FIG. 2b, exhibit the coming together or coapting of the free borders 28 of each leaflet 18 at meeting lines called commissures 30.

As is readily apparent from viewing FIG. 2a, if the normal circumference of annulus 22 becomes elongated so that the annulus 22 and physically related sinuses 26 (FIG. 2b) are dilated, leaflets 18 are unlikely to effect a sufficient closure, resulting in unacceptable regurgitation of blood from aorta 12 past commissures 30 and into ventricle 14. A prosthesis that restores the normal circumference of a dilated annulus 22 preferably will also not inhibit the natural movements experienced by the annulus 22 and surrounding tissues during compression (systole) and expansion (diastole) of the heart. In accordance with the teachings of the present invention, this restoration can best be accomplished by a flexibly semi-rigid prosthesis that is shaped to conform to the scalloped configuration of the annulus 22 and sinuses 26 combination in its normally undilated condition and is also provided with sufficient flexibility to permit the annular flexures of a regular cardiac cycle. Added strength for the prosthesis is achieved by providing suture anchoring points along legs 38 that correspond with the relatively more dense fibrous tissues in the vicinity of commissure 30 intersections with the aortic wall 20.

Exemplary apparatus of the present invention that achieve all of the preferred prosthetic characteristics are shown in FIGS. 1a and 1b which illustrate the infra-annular positioning of prosthesis 32A and the supra-annular positioning of prosthesis 32B, respectively. In FIG. 1a, prosthesis 32A is shown implanted below annulus 22 where it is sutured (not shown) to tissues within ventricle 14 below natural valve 10. FIG. 1b shows prosthesis 32B positioned above natural valve 10, anchored by sutures (not shown) to the walls of aorta 12, and descending into sinuses 26. Both embodiments include a flexible annular frame 34 having a scalloped configuration with projecting legs 38 circumferentially spaced to correspond with the location of aortic tissues either below or above the commissures 30 of valve 10. A symmetrical spacing of 120° between legs is generally adequate to accommodate the commissure locations of a trileaflet valve. Preferably, each frame is completely covered by a flexible biocompatible material 44 such as woven polyester, or other similarly strong and light material, coated or uncoated, to prevent exposure of the core frame of the prosthesis to living tissue or blood.

Prosthesis 32A is shown in FIG. 3 having upper wireform 35 of single wire construction. Wireform 35 is formed of flexibly semi-rigid metal, preferably an FDA approved nickel-cobalt alloy such as Elgiloy ® having its ends joined at coupling 36 by crimping, welding or other secure coupling process to form an uninterrupted ring having three axially projecting legs 38, one for each commissure 30 intersection of valve 10. Each leg 38 is joined to an adjacent leg by curved segments 40 generally following the contours of lower wireform 42, thus defining a circumferentially repetitive frame.

The frame 34 of the intra-annular prosthesis 32A in FIG. 3 exhibits scalloped upper 33a and lower 33b edges with peaks and valleys. The upper edge 33a is shaped to follow the contour of the tissue underneath the valve leaflets, and thus supports the leaflets and aortic wall from below. The lower edge 33b is similarly scallop-shaped, but with less pronounced peaks and valleys than the upper edge 33a. The lower edge 33b is thus shaped to conform to the aortic annulus shape and provide support directly thereto.

Lower wireform 42 is of similar single wire construction as upper wireform 35, and shaped to provide continuous reconstructive support along the entire circumference of the dilated valve annulus 22 when prosthesis 32A is implanted below valve 10 and adjacent to annulus 22. While the arcuate circumferential segments 40 of upper wireform 35 follow the beneficial scalloped shape of lower wireform 42, the primary function of upper wireform 35 is to provide anchoring support to lower wireform 42 when legs 38 are sutured to the denser tissues below each commissure 30 connection with aortic wall 20.

The relationship of upper and lower wireforms 35 and 42 is more clearly illustrated in the developmental lay-out flat pattern of prosthesis 32A illustrated in FIG. 4. Upper legs 38 are shown projecting at regular intervals in correspondence with dense tissue at the commissures that are generally spaced accordingly along the arterial wall, in order to provide anchoring strength to the prosthesis of FIG. 3. The arcuate circumferential segments 40 of upper wireform 35 are shown to be in close proximity with the similar circumferential segments 41 of lower wireform 42 along the substantial length of both wireforms, providing support for the annulus-restoring function of lower wireform 42. In this configuration, the peaks and valleys of the upper edge 33a are defined by legs 38 and circumferential segments 40 of upper wireform 35, and the peaks and valleys of the lower edge 33b are defined by lower wireform 42.

The two wireforms 35 and 42 are maintained in place relative to each other by a flexible biocompatible material 44 which also prevents living tissue and blood from making contact with the wireforms. The material 44 is preferably as thin as possible to minimize obstruction to the flow of blood through valve 10 and to reduce the overall bulk of prosthesis 32A. FIG. 5 taken along line 5—5 of FIG.3 is a cross-section of wireforms 35 and 42 at a point of minimum separation between them. Flexible material 44 is shown to provide the separation of the wireforms by the double-thickness of material at overlap 46 while maintaining the wireforms in proximity to each other along the length 48 of the material. Similarly, FIG. 6 is taken along line 6—6 of FIG. 3 and is a sectional view of the wireforms at a point of maximum separation, i.e., showing the tip of a projecting leg 38 and the associated wire form 42 positioned immediately below. The vertical separation between leg 38 and lower wireform 42 as shown in FIG. 6 is determined by the fixed height of leg 38 above arcuate segment 40 plus the distance between the wireforms 35 and 42 as illustrated in the developmental layout view of FIG. 4.

While the two-part wire form structure provides desirable anchoring strength via the upper wire form legs 38, and continuous reconstructive shape via the lower wireform 42 scalloped configuration, alternative single wall structures are within the scope of the present invention, provided they are light in weight and can accommodate a suturing needle. This can be accomplished either through the use of pre-formed holes or by fabricating the structure wall to facilitate piercing by the suturing needle. Suitable substances which may be utilized for fabricating such a single walled structure include strong, light-weight metals such as surgical steel, flexibly rigid plastics such as PTFE, and carbon fiber compositions.

FIG. 3a illustrates single-walled structure prosthesis 32C showing a typical suture 64 and preformed suturing holes 66 disposed about the surface of the structure to provide at least one such hole in each of its three widest portions corresponding to legs 38, and in each of its three narrowest portions corresponding to the arcuate segments 40 and 41 of prosthesis 32A. In the configuration of FIG. 3a, the upper edge 33a is defined by the upper contour of the single-walled prosthesis 32C, while lower edge 33b is defined by the lower contour of the single-walled prosthesis. The alternative walled structure 32C of FIG. 3a is surgically implanted below valve 10 in substantially the same manner as is the prosthesis 32A of FIG. 3, with at least one suture passed through each suturing hole 66.

Referring again to FIG. 1a, infra-annular embodiment 32A is put in place from above valve 10 by opening leaflets 18 against aortic wall 20 and lowering the prosthesis through the opened aortic aperture. Prosthesis 32A is then nested into the position shown in FIG. 1a by drawing tight the sutures (not shown) taken through fabric material 44 covering each leg 38 and each arcuate segment 40, 41 of the prosthesis. The sutures are also taken at corresponding tissue points below the commissures 30 and along the annulus 22, respectively, thereby securing each leg 38 and arcuate segment 40, 41 in place and observably restoring the dilated annulus to its normal circumference.

A more detailed illustration of the apparatus of FIG. 1b is shown as prosthesis 32B in FIG. 7. Because there is no continuous ring of tissue for suturing above leaflet attachment margin 24 (that is analogous to annulus 22 below margin 24), prosthesis 32B has no lower second ring, but instead is formed as a single wireform shaped to fit the contours of the sinuses 26.

In prosthesis 32B a single wire 50 drawn of a flexible metal such as nickel-cobalt alloy or stainless steel is formed into a wireform frame 34 having one axially projecting leg 38 for each commissure 30 intersection with arterial wall 20. A two-leaflet valve will produce one commissure, resulting in two intersections with the arterial wall at each end of the commissure. For a three leaflet valve, the legs 38 are shown spaced equally around the circumference of wireform 34 in FIG. 7 and in the developmental lay-out flat pattern of FIG. 8. Each leg 38 consists of an inverted U-shaped apex 54 and depending straight sections 56 which connect the opposite sides of each apex 54 to adjacent arcuate circumferential segments 41. The ends of wire 50 are joined in one such straight segment 56 at a coupling point or junction 60 by crimping, welding or other secure coupling process that does not substantially increase the diameter of the junction 60.

Since it is advantageous for the upper portion of prosthesis 32B to be more rigid (for effective constriction of abnormally dilated sinuses 26) relative to its lower portion (to avoid inhibiting normal movement of the same sinuses), wireform 34 is configured to achieve appropriate relative rigidity of these elements. For example, referring to FIG. 8, apices 54 and depending straight sections 56 may be of larger diameter or varying cross sectional thickness to be relatively more rigid than arcuate circumferential segments 41. Starting with a wire 50 diameter in the range of 0.020 to 0.040 inches, among the methods for effecting such stiffness is selectively electroplating apices 54 and straight sections 56 while leaving arcuate segments 41 untreated. Conversely, arcuate segments 41 may be etched to reduce their cross-sectional thickness thereby increasing their relative flexibility, or a combination of the foregoing treatments may be employed.

A flexible biocompatible material 44 covering all surfaces of wire frame 34 is partially illustrated in FIG. 7 and in the sectional view of FIG. 9. As described earlier, material 44 is preferably a strong, thin fabric such as polyester which separates the core structure of frame 34 from contact with bodily tissues and blood, and provides a sheath for suturing frame 34 in place without obstructing the flow of blood through valve 10. However, suitable alternative materials are within the scope of the present invention. For example knitted or bias weave polyesters, PTFE, or woven collagen fibers may all be used in accordance with the teachings of the present invention. The material 44 in FIG. 9 is configured as an elongated tube closely fitting around the wire 50. FIG. 10 illustrates an alternative configuration wherein the covering material 44 is a sheet and includes a pair of longitudinal edges 44a and 44b that are folded inward on themselves and sutured together around the wire 50.

To implant supra-annular prosthesis 32B, an incision is made in aorta 12 similar to that of the procedure for aortic valve replacement. Prosthesis 32B is lowered to the position shown in FIG. 1b so that circumferential segments 41 optimally fit into and restore the normal circumference of sinuses 26. Each leg 38 of prosthesis 32B is sutured in place to the tissues immediately above the intersection of one commissure 30 with the aortic wall 20, and other sutures taken as appropriate. The stiffness of legs 38 serves to prevent the sinus-correcting circumferential segments 41 from bowing outward, while the relatively less rigid segments 41 permit normal cardiac cycle flexures of sinuses 26 and annulus 22.

Those ordinarily skilled in the pertinent art will recognize that while known prostheses for atrioventricular mitral and tricuspid valves are unsatisfactory for arterial applications, the present invention is adaptable to atrioventricular use through the flexibility, compliance, anchoring strength and light-weight characteristics of its embodiments. In addition, any of the annular embodiments of this invention can be fabricated in a variety of diameters and angular placement of projections for custom fitting to the individual application. In general, a range of annular diameters between 17 mm and 29 mm will suffice for human implantation.

The foregoing description of an exemplary embodiment is not intended to imply a limitation on the invention, and no such limitation is to be inferred. The invention is intended to be limited only by the spirit and scope of the appended claims, which also provide a definition of the invention.

What is claimed is:

1. An annuloplasty prosthesis for infra-annular use in restoring the normal circumference of the dilated annulus and sinuses of a natural arterial heart valve having leaflets having a plurality of commissures, said prosthesis comprising:

an upper edge having a plurality of axially projecting legs, each of said legs corresponding to the location of a commissure of said valve and being sequentially interconnected by arcuate circumferential segments of said upper edge, the upper edge thus defining a series of peaks and valleys;

a lower edge disposed below and substantially adjacent to said upper edge and shaped to conform to the peaks and valleys of upper edge, the lower edge defining a series of peaks and valleys which is less pronounced than that of the upper edge; and a flexible biocompatible material covering the prosthesis.

2. The prosthesis of claim 1 comprising:

an upper wireform forming the upper edge; and a lower wireform forming the lower edge.

3. The prosthesis of claim 1 wherein said upper and lower wireforms are spaced apart and only connected by the flexible biocompatible material covering.

4. The prosthesis of claim 1 wherein said upper and lower wireforms are metallic.

5. The prosthesis of claim 4 wherein said upper and lower wireforms are formed of nickel-cobalt alloy.

6. The prosthesis of claim 1 wherein the upper and lower edges are defined by a single-walled structure adapted to be pierced by a suturing needle.

7. The prosthesis of claim 6 wherein said single-walled structure has a plurality of suturing holes disposed about its surface.

8. The prosthesis of claim 7 wherein said single-walled structure is metallic.

9. The prosthesis of claim 6 wherein said single-walled structure is plastic.

10. The prosthesis of claim 1 wherein said biocompatible material is woven polyester.

11. A method for restoring the normal circumference of a dilated annulus of a natural arterial heart valve having a plurality of leaflets and commissures under the valve leaflets intersecting with an aortic wall, said method comprising;

providing an infra-annular ring prosthesis including a flexible portion having arcuate segments dimensioned to conform to said normal circumference of said heart valve annulus, an anchoring portion including a plurality of axially projecting legs, each of said legs dimensioned to conform to respective commissures, and a flexible biocompatible covering material;

inserting said infra-annular prosthesis from above said valve through an aperture formed by the opening of said valve leaflets;

positioning said prosthesis below said valve adjacent to said annulus and below said commissures with each of said legs disposed adjacent to respective commissures; and suturing each of said legs in place.

* * * * *

UNITED STATES PATENT AND TRADEMARK OFFICE
CERTIFICATE OF CORRECTION

PATENT NO. : 6,231,602 B1
DATED : May 15, 2001
INVENTOR(S) : Alain Carpentier, Hung Ly Lam, Than Nguyen It is certified that error appears in the above-identified patent and that said Letters Patent is hereby corrected as shown below:

Claim 1,
Line 7, after "valleys" insert -- that follow the contour of the tissue underneath the valve leaflets --

Claim 11,
Line 8, after "commissures" insert -- under the valve leaflets --

Signed and Sealed this

Fifth Day of March, 2002

Attest:

JAMES E. ROGAN
Attesting Officer
Director of the United States Patent and Trademark Office